(12) United States Patent
Ryan et al.

(10) Patent No.: US 11,357,952 B2
(45) Date of Patent: Jun. 14, 2022

(54) METHOD OF MAKING A READY-TO-USE CATHETER ASSEMBLY AND A READY-TO-USE CATHETER ASSEMBLY

(71) Applicant: Teleflex Life Sciences PTE. LTD., Singapore (SG)

(72) Inventors: Katy Ryan, Cork (IE); Ronald John Kelly, Oranmore (IE); Morgan Tierney, Tullamore (IE); David Scully, Tullamore (IE); Alan Fitzgerald, Edgeworthstown (IE)

(73) Assignee: TELEFLEX LIFE SCIENCES PTE. LTD., Singapore (SG)

( * ) Notice: Subject to any disclaimer, the term of this patent is extended or adjusted under 35 U.S.C. 154(b) by 1028 days.

(21) Appl. No.: 15/604,910

(22) Filed: May 25, 2017

(65) Prior Publication Data
US 2017/0340857 A1   Nov. 30, 2017

(30) Foreign Application Priority Data
May 25, 2016 (EP) .................................. 16001196

(51) Int. Cl.
*A61M 5/32* (2006.01)
*A61M 25/00* (2006.01)
(Continued)

(52) U.S. Cl.
CPC ............. *A61M 25/002* (2013.01); *A61L 2/08* (2013.01); *A61L 2/087* (2013.01);
(Continued)

(58) Field of Classification Search
CPC .......... A61M 5/32; A61M 1/00; A61M 27/00; A61M 25/002; A61F 5/44; A61B 19/00; A61B 50/30; A61L 2/0029–2/0076
See application file for complete search history.

(56) References Cited

U.S. PATENT DOCUMENTS 4,364,929 A * 12/1982 Sasmor .................. A61K 31/74
424/667
5,226,530 A * 7/1993 Golden ............... A61M 25/002
206/210
(Continued)

FOREIGN PATENT DOCUMENTS

WO 94/26337 A1 11/1994
WO 00/30696 A1 6/2000
(Continued)

*Primary Examiner* — Tatyana Zalukaeva
*Assistant Examiner* — Ilya Y Treyger
(74) *Attorney, Agent, or Firm* — BakerHostetler

(57) ABSTRACT

A method of making a ready-to-use catheter assembly is provided, which can be immediately used by a patient. The ready-to-use catheter assembly ensures that the catheter does not suffer from a loss of quality during its shelf life and a wetting medium are provided. The method comprises: placing a catheter with an inactivated hydrophilic outer surface at least along its insertable length and a wetting medium in a catheter package; treating the catheter package with the catheter and the wetting medium with electro-magnetic and/or particle radiation while at least initially the hydrophilic outer surface at least along the insertable length of the catheter remains inactivated; and activating the hydrophilic outer surface at least along the insertable length of the catheter with the wetting medium during and/or after the radiation treatment and wherein the wetting medium decreases in viscosity when submitted to electro-magnetic and/or particle radiation.

5 Claims, 10 Drawing Sheets

(51) Int. Cl.
*A61L 2/08* (2006.01)
*A61M 25/01* (2006.01)
*A61M 1/00* (2006.01)
*A61M 27/00* (2006.01)
*A61F 5/44* (2006.01)

(52) U.S. Cl.
CPC .... *A61M 25/0009* (2013.01); *A61M 25/0017* (2013.01); *A61M 25/0045* (2013.01); *A61M 25/0111* (2013.01); *A61L 2202/24* (2013.01); *A61M 27/00* (2013.01); *A61M 2025/0046* (2013.01); *A61M 2025/0062* (2013.01)

(56) References Cited

U.S. PATENT DOCUMENTS

| | | | |
|---|---|---|---|
| 5,749,837 A | 5/1998 | Palermo et al. | |
| 6,053,905 A * | 4/2000 | Daignault, Jr. | A61M 25/0111 206/364 |
| 6,102,898 A | 8/2000 | Khan et al. | |
| 6,409,717 B1 * | 6/2002 | Israelsson | A61F 5/44 604/544 |
| 6,602,244 B2 * | 8/2003 | Kavanagh | A61M 25/002 604/172 |
| 7,959,857 B2 * | 6/2011 | Freeman | A61L 2/087 422/22 |
| 8,282,624 B2 * | 10/2012 | Tanghoej | A61M 25/0017 604/163 |
| 9,550,005 B2 * | 1/2017 | Lin | A61L 2/10 |
| 9,808,596 B2 * | 11/2017 | Tomes | A61M 25/002 |
| 2001/0001443 A1 * | 5/2001 | Kayerod | A61L 29/085 206/364 |
| 2005/0109648 A1 | 5/2005 | Kerzman et al. | |
| 2005/0137582 A1 | 6/2005 | Kull-Osterlin et al. | |

FOREIGN PATENT DOCUMENTS

| | | |
|---|---|---|
| WO | 00/47494 A1 | 8/2000 |
| WO | 2006/117372 A1 | 11/2006 |
| WO | 2007/137699 A1 | 12/2007 |
| WO | 2012/085107 A2 | 6/2012 |
| WO | 2014/063711 A1 | 5/2014 |
| WO | 2014/074141 A1 | 5/2014 |
| WO | 2014/135168 A2 | 9/2014 |
| WO | 2015/075141 A1 | 5/2015 |

* cited by examiner

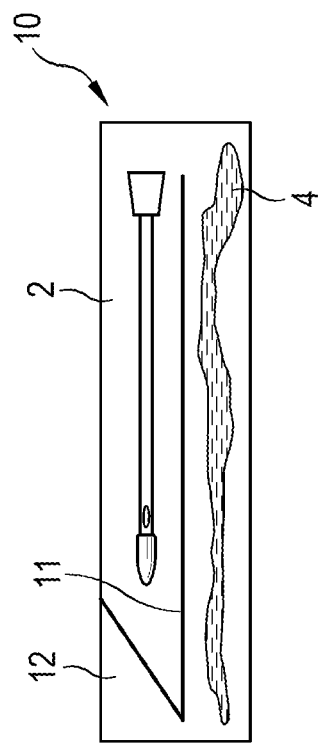
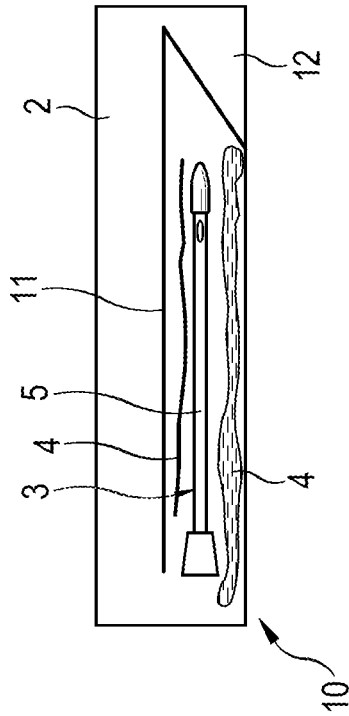
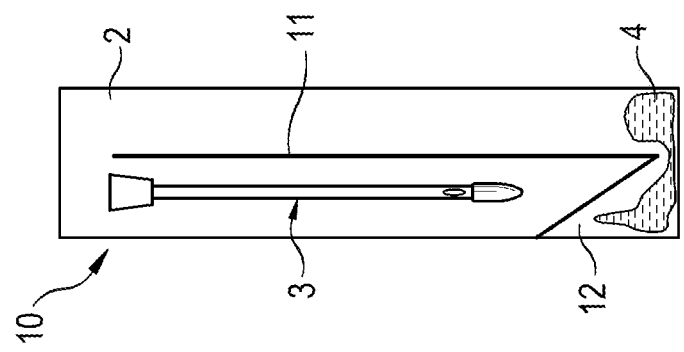
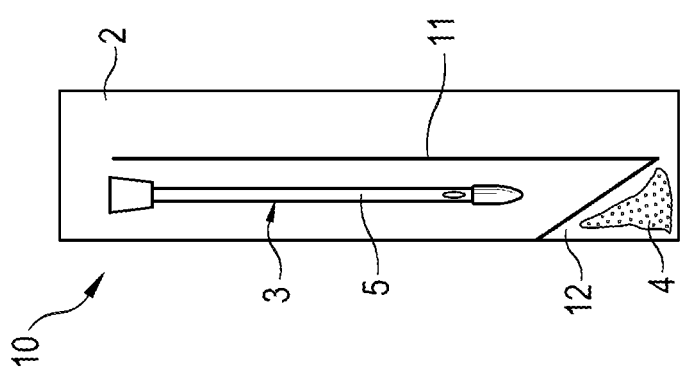

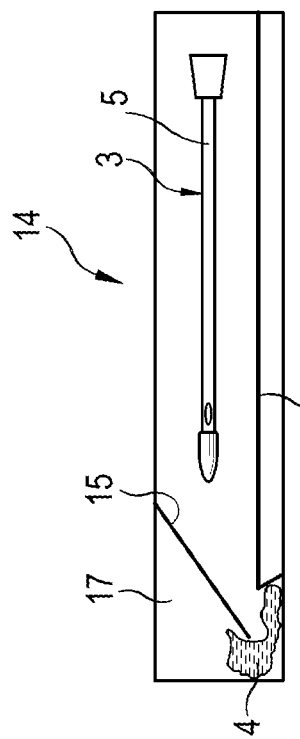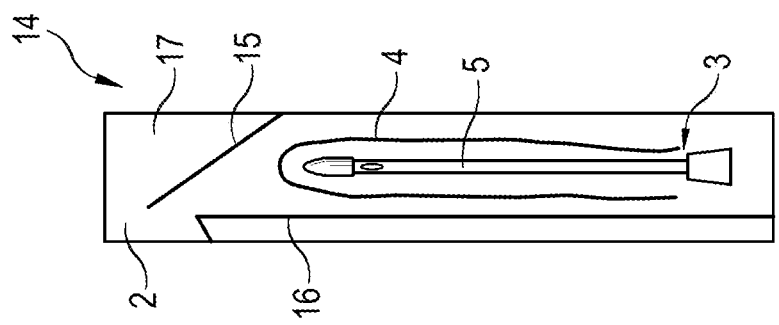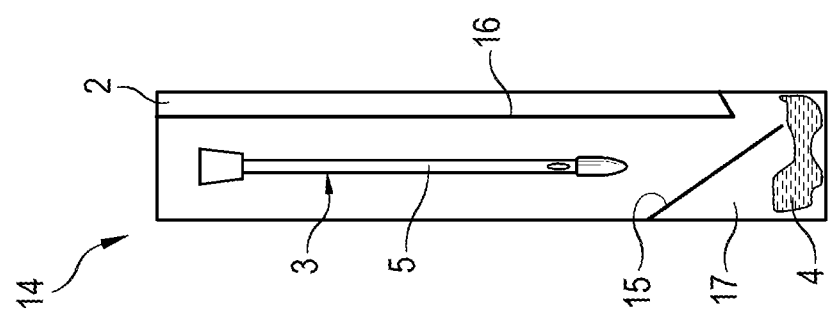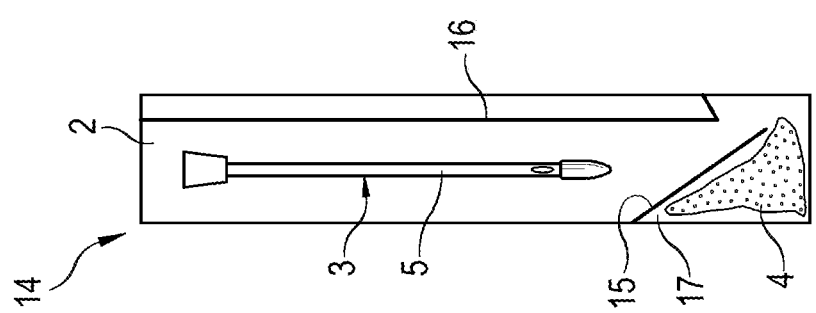
Fig. 3c
Fig. 3d
Fig. 3b
Fig. 3a

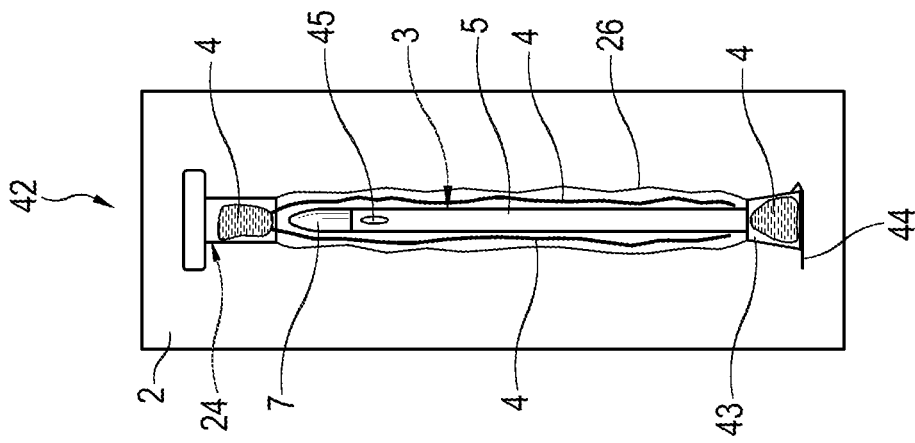
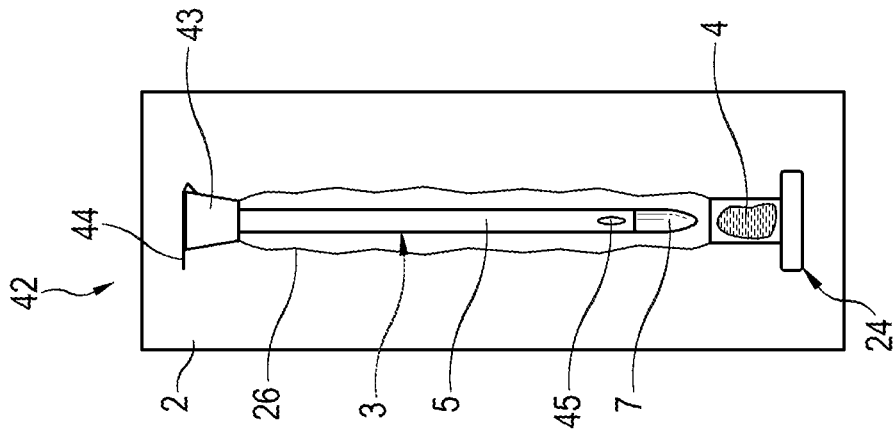
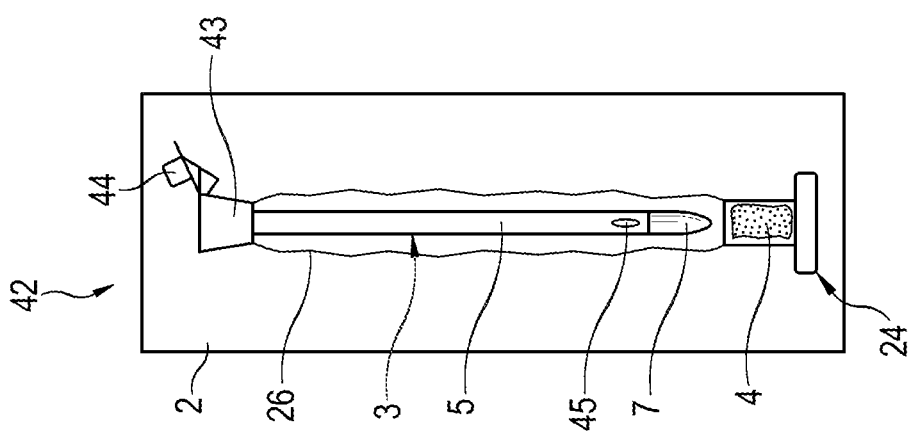

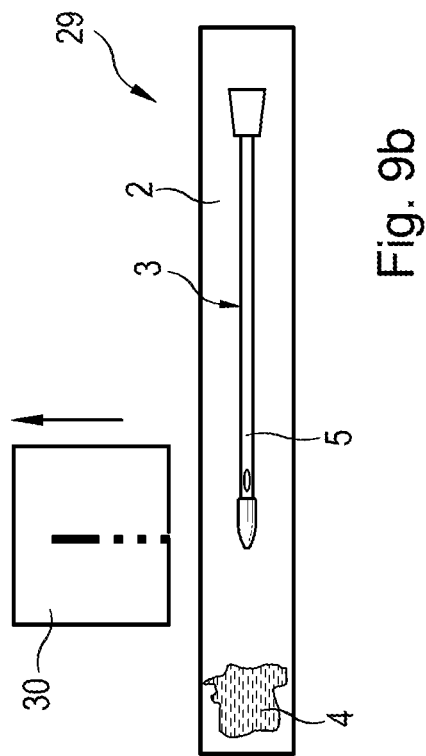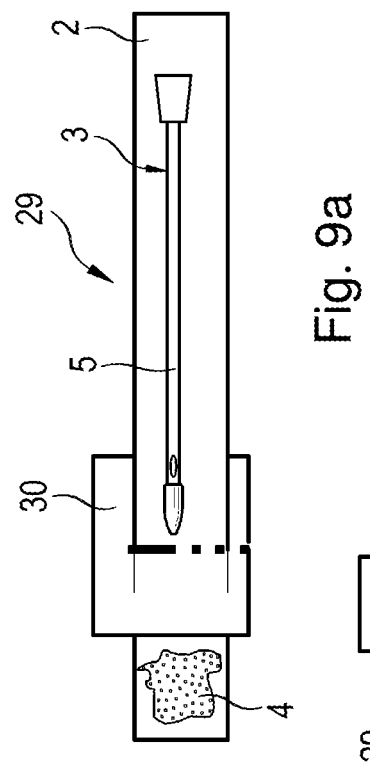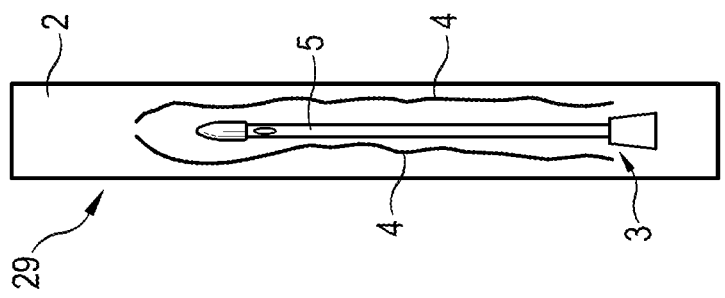

METHOD OF MAKING A READY-TO-USE CATHETER ASSEMBLY AND A READY-TO-USE CATHETER ASSEMBLY

CROSS-REFERENCE TO RELATED APPLICATION

This application claims priority to foreign European patent application No. EP 16001196.1, filed on May 25, 2016, the disclosure of which is incorporated by reference in its entirety.

FIELD OF THE INVENTION

The present patent application refers to a method of making a ready-to-use catheter assembly, a catheter assembly for use in the method, a ready-to-use catheter assembly and the use of a wetting medium in the method.

BACKGROUND

Such ready-to-use catheter assemblies are usually used for intermittent catheterization by patients who are unable to empty their bladder naturally. The bladder is then emptied in regular intervals by the patients themselves using a urinary catheter. Urinary catheters are usually provided with a surface treatment using a lubricant to reduce friction in order to allow for an easier and less traumatic insertion into the urethra. Currently, there are two major categories of catheters having lubricated surfaces, namely, gel-coated catheters and hydrophilic coated catheters.

Gel-coated catheters are made easier to insert by application of a water-based gel to the catheter surface. Typically, this gel is supplied with the packaged catheters and a system is provided with the packaged catheters to apply the gel to the surface of the catheters. The gel can either be put onto the catheter surface just before or during the packaging operation or the gel is applied to the surface of the catheter as the catheter is inserted by the patient.

In a hydrophilic coated catheter, the catheter is provided with a hydrophilic coating which is adhered to the outer surface of the catheter. Before insertion of the catheter, the hydrophilic coating is activated by swelling in contact with a hydrating liquid such as water. The catheter surface then has an extremely low coefficient of friction. There exist different systems for hydrophilic coated catheters. It is known that a sterile, individually packed single use catheter is provided in a dry state or condition. The patient opens the package, pours water into the package, waits for approximately thirty seconds and then removes the catheter from the package, which is now ready for insertion. In another version of the hydrophilic coated catheter, the catheter is provided in a package that already contains enough loose liquid water to cause the catheter to be immersed. The user then simply opens the package and removes the catheter which is ready for insertion without the need to add water or to wait. Other products provide the amount of liquid necessary for the immersion of the catheter in a separate compartment of the package or in a sachet arranged in the package. With these products, the user must open a separate compartment of the package or the sachet allowing the liquid to enter the catheter containing chamber for activating the hydrophilic coated surface.

In order to reduce the risk of infections in the urinary tract due to intermittent catheterization, the urinary catheters as well as the wetting media used need to be sterilized. The sterilization of medical devices is usually performed at the time of manufacture using techniques which are well known in the art as for example radiation such as beta radiation or gamma radiation. However, sterilization of a catheter such as an intermittent urinary catheter with a hydrophilic coating is generally regarded as cumbersome if not impossible using conventional techniques. Radiation sterilization of a catheter with a hydrophilic coating has the well known problem that an undesirable chemical modification of said coating occurs, decreasing the quality of the coating which may lead to an increase of the coefficient of friction.

It is therefore known to add one or more buffers, antioxidants, or other additives to the wetting fluids to prevent ruining the coating of the catheter during radiation sterilization. Furthermore, it is also known to add hydrophilic polymers to the wetting solution, wetting the hydrophilic coating of the catheter with this polymer solution and to then sterilize the wet or activated hydrophilic coated catheter using radiation.

A further method of preparing a ready-to-use urinary catheter and a catheter assembly for use are disclosed in WO 2014/063711 A1. In this method, a catheter assembly is provided which comprises a first compartment in which a catheter with a hydrophilic coating is placed and a second compartment which comprises the liquid swelling medium. The catheter assembly is then sterilized and after sterilization, the liquid swelling medium is added to the first compartment for wetting and activating the catheters' exterior coating. After that, the second compartment is removed from the catheter assembly.

SUMMARY OF THE INVENTION

It is an object of the present patent application to provide alternative solutions for making a ready-to-use urinary catheter and a ready-to-use catheter assembly in which the catheter can be stored for its maximum shelf life without suffering any losses to quality, especially to its hydrophilic coating so that the catheter can be safely inserted into the urethra of the patient without causing discomfort. Furthermore, the method and the catheter assembly itself should be simple and cost effective.

These objects are achieved by a method of making a ready-to-use catheter assembly comprising the following steps:

Placing a catheter with an inactivated hydrophilic outer surface at least along its insertable length and a wetting medium in a catheter package;

Treating the catheter package with the catheter and the wetting medium with electro-magnetic or particle radiation while at least initially the hydrophilic outer surface at least along the insertable length of the catheter remains substantially inactivated;

Activating the hydrophilic outer surface at least along the insertable length of the catheter with the wetting medium during and/or after the radiation treatment; wherein the wetting medium decreases in viscosity when submitted to electro-magnetic and/or particle radiation.

The outer surface of the catheter is the surface of the catheter which potentially comes into contact with human tissue when being inserted into the urethra of a patient. In order to reduce the friction between the catheter and the urethra, this outer surface is hydrophilic at least along its insertable length and therefore very slippery when activated by a wetting medium. In order to obtain the hydrophilic outer surface, the catheter can be coated with a hydrophilic coating or the entire catheter shaft can be made of a hydrophilic material.

The term "insertable length" means the length of the catheter shaft which comes into contact with the human tissue when the catheter is inserted into the urethra of a patient. Due to the many different anatomical structures, it is not possible to define an exact length of the insertable length. Typically, the insertable length of catheters used by male patients lies in a range from approximately 30-40 cm and for female users in a range of approximately 10-20 cm.

The catheter package can be made of a material with low moisture transmission. This means that the package is made of a material that keeps at least an amount of wetting medium inside the catheter package that is large enough to keep the hydrophilic outer surface of the catheter in the activated state for the shelf life of the catheter assembly. Typically, the shelf life of a catheter assembly lies in a range from thirty six months to five years. Examples for a material with low moisture transmission which can be used for the catheter package are composite or multi-laminated materials consisting of aluminum foil, LDPE, MDPE, HDPE, LLDPE or blends of the afore, PP, polyester based polymers (PET), of siloxane coatings. However, it is also possible to provide other methods for keeping the hydrophilic outer surface at least along the insertable length of the catheter in the activated state for the shelf life of the catheter assembly.

Before the treatment with electro-magnetic and/or particle radiation (the radiation treatment), the wetting medium has a high viscosity. Due to the high viscosity, the wetting medium stays in the catheter package at the place where it has been inserted and does not tend to flow towards the catheter. Therefore, the risk for an accidental wetting of the outer surface of the catheter and therefore the risk of activating the hydrophilic material before the radiation treatment is very low. When the catheter assembly with the catheter and the wetting medium is submitted to energy during the radiation treatment the viscosity of the wetting medium decreases. The wetting medium thus comes in a low viscosity state and can easily be brought into contact with the hydrophilic outer surface of the catheter. This can be done by tilting or turning the catheter package around a specific angle, as for example an angle of approximately 90° or 180°. The wetting medium can be any liquid which reduces its viscosity when external conditions are changed. Examples for such liquids are viscoelastic fluids, Bingham fluids, pseudoplastic fluids, dilatant fluids or Newtonian fluids. Furthermore, the wetting medium can be a gel. It is also possible to use a wetting medium which is initially a solid and changes its state of matter during the radiation treatment from the solid state to the liquid state.

In a preferred variant of the method, the electromagnetic and/or particle radiation treatment is a sterilizing step for sterilizing the catheter assembly with the catheter and the wetting medium placed in the catheter package. In this case, no additional production step is necessary.

Preferably, the viscosity of the wetting medium decreases by at least 80%, more preferably at least 90%, when submitted to electro-magnetic and/or particle radiation. In this way, it can be ensured that the wetting medium has a sufficiently low viscosity after the radiation treatment so that an easy activation of the hydrophilic outer surface of the catheter is possible.

In a variant of the method, the wetting medium is a gel comprising at least one polymer. In this context, the term "gel" refers to gels, hydrogels, high viscous aqueous solutions which contain a polymer or a thixotropic agent. Tests have shown that such gels degrade when submitted to radiation sterilization and transform into the desired aqueous fluid solution. This aqueous fluid solution allows easy activation of the hydrophilic outer surface of the catheter.

Preferably, the gel has a viscosity of at least 7000 cP, preferably at least 25000 cP, before the radiation treatment. In this case, the viscosity of the wetting medium before the radiation treatment is high enough to enable an easy separation between the wetting medium and the hydrophilic outer surface at least along the insertable length of the catheter. During the radiation treatment, the wetting medium degrades sufficiently, so that it can be easily brought into contact with the hydrophilic outer surface at least along the insertable length of the catheter for activating this surface due to its fluid nature.

In a further embodiment, the polymer is organic or synthetic carbohydrate or a liquid based polymer. Such a gel combines the desired high viscosity before the radiation treatment and the requested liquid properties for activating the hydrophilic outer surface at least along the insertable length of the catheter after being submitted to electro-magnetic and/or particle radiation.

In a further variant of the method, the radiation used for the radiation treatment is gamma radiation, x-ray, e-beam or UV. This leads to a sterile state of the whole catheter assembly and also ensures that sufficient energy is delivered to the wetting medium so that the wetting medium transforms into the aqueous solution during the radiation treatment.

Tests have shown that the best results can be achieved when the energy dose of the radiation is in a range of 1 to 50 kGy, preferably 15 to 45 kGy, more preferably 25 to 45 kGy. With such an energy dose, no damage to the catheter is incurred and the wetting medium degrades and turns into the aqueous liquid.

In still another variant, the catheter package used in the method can comprise an open channel diversion for separating the catheter with the hydrophilic outer surface at least along its insertable length and the wetting medium from each other before and during the radiation treatment. For example, the catheter package can be provided with at least one welding seam which forms a back taper in the package and in which the wetting medium is arranged. In a variant, the catheter with the hydrophilic outer surface at least along its insertable length and the wetting medium can be separated by a physical barrier. The open channel diversion and the physical barrier ensure that the hydrophilic outer surface at least along the insertable length of the catheter and the wetting medium do not come into contact before and during the radiation treatment which could lead to a degradation of the hydrophilic outer surface.

It can be further provided that the catheter is surrounded by a sleeve. Due to this sleeve, the patient can easily grip and insert the activated slippery catheter.

In a further variant of the method, it can be provided that the wetting medium is partially a gel and partially an aqueous solution. The gel forms a plug which holds the aqueous solution in a cavity so that it does not come into contact with the hydrophilic outer surface of the catheter before and during the radiation treatment. During the radiation treatment, the gel experiences a decrease in viscosity so that the activation of the hydrophilic outer surface at least along its insertable length of the catheter can be easily performed after the radiation treatment. In this case, a viscosity decrease of just 10% would be sufficient, because the plug only needs to dislocate to let the aqueous solution pass.

It is a further object of the present invention to provide a catheter assembly for use in a method as described above.

The catheter assembly comprises a catheter package, a catheter with an inactived hydrophilic outer surface at least along its insertable length arranged in the catheter package, and a wetting medium arranged in the catheter package, whereby the wetting medium decreases in viscosity when submitted to electro-magnetic and/or particle radiation. The catheter assembly therefore allows an easy and secure separation between at least the insertable length of the hydrophilic outer surface of the catheter and the wetting medium before and at least initially during the treatment with electro-magnetic and/or particle radiation, and an easy activation of the hydrophilic outer surface of the catheter during and/or after the radiation treatment when the wetting medium has experienced the decrease in viscosity.

In a preferred embodiment, the wetting medium is at least partially a gel with a viscosity of at least 7000 cP, preferably at least 25000 cP, before the radiation treatment. Due to the high viscosity, the gel is immobilized in the catheter package and does not come into contact with the hydrophilic outer surface at least along the insertable length of the catheter before and at least initially during the radiation treatment.

Additionally, it can be provided that the catheter package comprises an open channel diversion for separating the catheter with the hydrophilic outer surface at least along its insertable length and the wetting medium from each other before and during the radiation treatment. The open channel diversion is an additional safeguard to avoid contact between the wetting medium and the hydrophilic outer surface at least along its insertable length of the catheter before and at least initially during the radiation treatment which could damage the hydrophilic outer surface of the catheter and could cause problems when inserting the catheter. Due to the open channel structure, a contact between the outer surface of the catheter and the wetting medium is easily possible after the radiation treatment when the wetting medium has experienced the decrease in viscosity.

It is also possible to provide the catheter package with at least one welding seam which forms a back taper in the package in which the wetting medium is arranged. This is an easy and economic way to provide an open channel diversion structure in the catheter package which can be easily integrated in the production process of the catheter assembly. The back taper retains the wetting medium before and during the radiation treatment. After the radiation treatment, the low viscous wetting medium can easily flow out of the back taper to the catheter to activate the hydrophilic outer surface at least along the insertable length of the catheter.

To ensure a very secure separation between the hydrophilic outer surface at least along the insertable length of the catheter and the wetting medium, it can be provided that the catheter with the hydrophilic outer surface at least along its insertable length and the wetting medium are separated by a physical barrier. Such a barrier can, for example, be a clip or another fastener device.

In still another embodiment, the catheter package comprises a perforated lining which is arranged between the catheter with the hydrophilic outer surface at least along its insertable length and the wetting medium. The high viscosity wetting medium is then held back by the perforated lining during the radiation treatment and can pass through the perforated lining during and/or after the radiation treatment when it has degraded into an aqueous solution with low viscosity. Such a perforated lining can be achieved by welding during the manufacture process and is therefore easy and cost effective. When necessary, external pressure can be applied onto the part of the catheter package behind the perforated lining to squeeze the wetting medium in to the catheter compartment.

In another embodiment, at least a part of the catheter is surrounded by a sleeve. This sleeve can be used as an introduction aid to insert the activated and thus very slippery catheter into the urethra. Furthermore, the sleeve can be arranged around the external end of the catheter before use so that the wetting medium does not come into contact with these parts of the catheter.

Furthermore, it can be provided that the wetting medium is partially an aqueous solution and partially a gel which forms a plug to separate the aqueous solution from the catheter with the hydrophilic outer surface at least along its insertable length. This is another way to ensure that the hydrophilic outer surface of the catheter and the wetting medium are kept separate before and at least initially during the radiation treatment of the catheter assembly to avoid degradation of the hydrophilic parts of the catheter which would cause problems during the use of the catheter assembly.

Furthermore, the catheter assembly can comprise an insertion aid for the catheter which is preferably arranged near the catheter tip. The insertion aid can be a cylindrical part which can be easily gripped by the patient. In this case, the wetting medium is preferably arranged in the insertion aid. After the radiation treatment, the catheter assembly is simply rotated around 180° and the wetting medium then flows out of the introduction aid and along the catheter shaft to activate the hydrophilic outer surface at least along the insertable length of the catheter.

It is a further object of the present invention to provide a ready-to-use catheter assembly which can be directly used by a patient without the need for activation and wherein the low friction properties of the catheter do not degrade during storage so that a complication-free introduction of the catheter into the urethra is guaranteed during its whole shelf life which ranges from approximately thirty six months to five years. This is achieved by a ready-to-use catheter assembly which comprises a catheter package, a catheter with a hydrophilic outer surface at least along its insertable length arranged in the catheter package and a wetting medium which is also arranged in the catheter packing and which is in contact with the hydrophilic outer surface of the catheter so that the hydrophilic outer surface is activated, wherein the wetting medium is a gel comprising at least one polymer and has a viscosity below 1000 cP, preferably below 100 cp.

The ready-to-use catheter assembly therefore comprises a pre-activated catheter which can be directly used by the patient. The patient does not have to perform any activating steps which are often cumbersome to perform by a person with reduced dexterity. Furthermore, due to the fact that the activation has been performed during the manufacturing process, it can be guaranteed that the activation has been performed properly and the catheter has a sufficiently slippery surface along the complete insertable length thereof. Therefore, no problems due to high friction occur during the use of the catheter. The desired low viscosity of the wetting medium is achieved by submitting the wetting medium to a radiation treatment where the wetting medium degrades to an aqueous solution.

It is still a further object of the present invention to provide an easy and secure method to activate a hydrophilic coated catheter. This object is achieved by using a wetting medium for activating the hydrophilic outer surface at least along the insertable length of the catheter whereby the wetting medium experiences a decrease in viscosity when submitted to electro-magnetic and/or particle radiation.

BRIEF DESCRIPTION OF THE DRAWINGS

In the following, the invention is described in more detail with the aid of figures.

FIG. 2a shows a second embodiment of a catheter assembly before a treatment with electro-magnetic and/or particle radiation, FIG. 2b shows the catheter assembly of FIG. 2a after the radiation treatment and before activation of the hydrophilic outer surface of the catheter, FIGS. 2c and 2d show the catheter assembly of FIG. 2a during activation of the hydrophilic outer surface of the catheter, FIG. 3a shows a third embodiment of a catheter assembly before a treatment with electro-magnetic and/or particle radiation, FIG. 3b shows the catheter assembly of FIG. 3a after the radiation treatment and before activation of the hydrophilic outer surface of the catheter, FIGS. 3c and 3d show the catheter assembly of FIG. 3a during activation of the hydrophilic outer surface of the catheter, FIG. 7a shows a seventh embodiment of a catheter assembly before a treatment with electro-magnetic and/or particle radiation, FIG. 7b shows the catheter assembly of FIG. 7a after the radiation treatment and before activation of the hydrophilic outer surface of the catheter, FIG. 7c shows the catheter assembly of FIG. 7a during activation of the hydrophilic outer surface of the catheter, FIG. 9a shows a ninth embodiment of a catheter assembly before a treatment with electro-magnetic and/or particle radiation, FIG. 9b shows the catheter assembly of FIG. 9a after the radiation treatment and before activation of the hydrophilic outer surface of the catheter, FIG. 9c shows the catheter assembly of FIG. 9a during activation of the hydrophilic outer surface of the catheter.

DETAILED DESCRIPTION

Figure 1C:
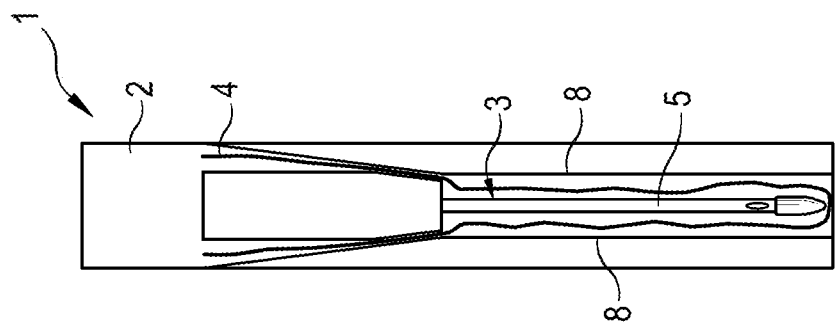
FIG. 1c shows the catheter assembly of FIG. 1a during activation of the hydrophilic outer surface of the catheter.
Figure 1B:
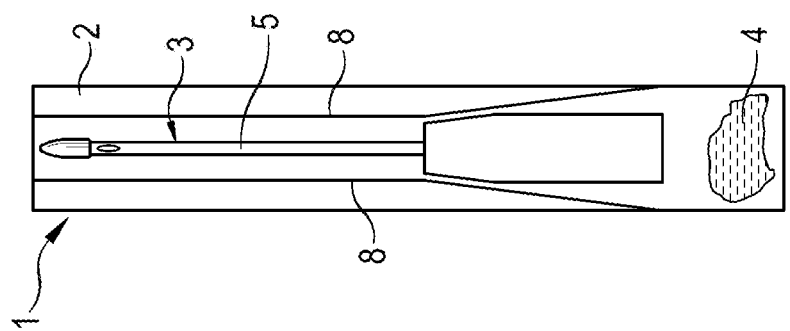
FIG. 1b shows the catheter assembly of FIG. 1a after the radiation treatment and before activation of the hydrophilic outer surface of the catheter.
Figure 1A:
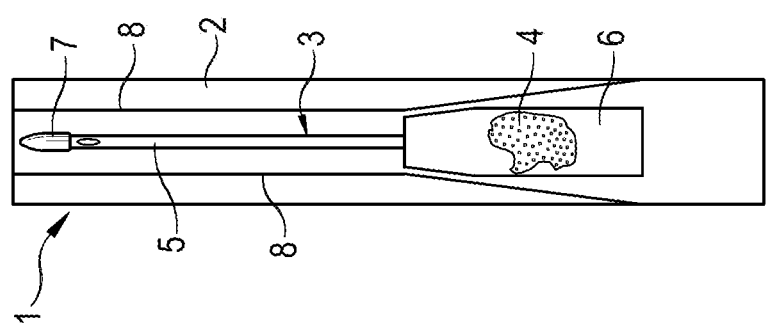
FIG. 1a shows a first embodiment of a catheter assembly before a treatment with electro-magnetic and/or particle radiation.

FIG. 1a shows a catheter assembly 1 according to the present invention before a treatment with electro-magnetic and/or particle radiation (the radiation treatment). The catheter assembly 1 comprises a catheter package 2, a catheter 3 and a wetting medium 4. The catheter 3 and the wetting medium 4 are arranged inside the catheter package 2. The catheter package 2 is preferably made of an endless film tube which can for example be sealed at both ends. The film tube does not comprise any seams along its longitudinal direction. The catheter package is preferably made of a material that has a low moisture transmission. Examples for materials that can be used are composite or multi-laminated materials comprising materials of aluminum foil, LDPE, MDPE, HDPE, LLDPE or blends of the afore, PP, polyester based polymers (PET), or siloxane coatings.

The wetting medium 4 experiences a decrease in viscosity when submitted to electro-magnetic and/or particle radiation. For example, the wetting medium can be a gel. In the context of the present patent application, the term "gel" refers to gels, hydrogels, and any high viscous aqueous solutions which contain a polymer or a thixotropic agent. FIG. 1a shows the catheter assembly 1 before the radiation treatment. Therefore, the wetting medium 4 is still in the form of a relative solid exhibiting little or no viscous flow.

The catheter 3 comprises an inactivated hydrophilic outer surface 5 at least along its insertable length. The catheter 3 and the wetting medium 4 are arranged in the catheter package 2 in such a way that the hydrophilic outer surface 5 remains substantially inactivated. In the present case the wetting medium 4 does not come into contact with at least the hydrophilic outer surface 5 of the catheter 3. As the wetting medium is relatively solid and exhibits little or no viscous flow, it stays at the position in which it has been placed and does not flow in the direction of the hydrophilic outer surface 5 of the catheter 3.

The catheter assembly 1 further comprises a sleeve 6. The sleeve 6 surrounds the catheter 3 and is placed at the external end of the catheter 3 which lies opposite the catheter tip 7. At its end facing away from the catheter 3, the sleeve 6 is folded so that the wetting medium 4 cannot enter the sleeve 6.

FIG. 1c shows the catheter assembly 1 in the activated state. In the activated state, the wetting medium 4 has dissociated due to electro-magnetic and/or particle radiation and now forms a low viscosity solution which flows along the catheter 3, thereby coming into contact with the hydrophilic outer surface 5 at least along the insertable length of the catheter 3 and thus activating the hydrophilic outer surface 5. As can be seen in FIGS. 1a to 1c, the catheter package 2 comprises two welding seams 8 on each side of the catheter. These welding seams 8 taper towards the tip of the catheter 3 and thus guide the wetting medium 4 in its aqueous state along the longitudinal direction of the catheter 3.

FIG. 2a shows a second embodiment of a catheter assembly 10. The same elements as in the previous embodiment are described with the same reference numbers. In this and the following embodiments, only the differences to the other embodiments are described. The catheter assembly 10 comprises a catheter package 2, a catheter 3 arranged in the catheter package 2 and a wetting medium 4 also arranged in the catheter package 2. The catheter package 2 further comprises a welding seam 11 which forms a back taper 12 in the catheter package 2. In this back taper 12, the wetting medium 4 is arranged. As the wetting medium 4 is still in its high viscosity, relatively solid state with little or no viscous flow, it remains in this back taper 12.

FIG. 2d shows the catheter assembly 10 of FIG. 2a after the radiation treatment and during activation of the hydrophilic outer surface 5 of the catheter 3. The wetting medium 4 is now in its low viscosity state and is an aqueous solution which can freely flow through the catheter package 2. The wetting medium 4 has therefore left the back taper 12 which is formed by the welding seam 11, flows around the catheter 3 and is in contact with the hydrophilic outer surface 5 at least along the insertable length of the catheter 3 and activates the hydrophilic outer surface 5 of the catheter 3. The catheter package 2 is still completely closed so that the activated catheter 3 can be stored in sterile conditions.

FIG. 3a shows a third embodiment of a catheter assembly 14. The same reference numbers are used for the same elements as described in the two previous embodiments. The catheter assembly 14 comprises a catheter package 2, a catheter 3 arranged in the catheter package 2 and a wetting medium 4 also arranged in the catheter package 2. The catheter package 2 comprises two welding seams 15 and 16. The first welding seam 15 extends transverse to the longitudinal direction of the catheter package 2 and comprises an angle of approximately 45° with the longitudinal direction of the catheter package 2. The welding seam starts at one side of the catheter package and ends before the second side of the catheter package 2. Therefore, a back taper 17 is formed by this first welding seam 15. In this back taper 17, the wetting medium 4 is placed. As the wetting medium 4 is in its relatively solid state, it remains in the back taper 17 and does not flow in the direction of the catheter 3. The second welding seam 16 is arranged near the opposite side of the catheter package 2 and extends along the longitudinal direction of the catheter 3. This second welding seam 16 forms a neck in the catheter package 2 so that the catheter 3 is arranged in a relatively narrow passage of the catheter package 2.

FIG. 3d shows the catheter assembly 14 of FIG. 3a after the radiation treatment and during the activation of the hydrophilic outer surface 5 of the catheter 3. The wetting medium 4 is now in its low viscosity state and is an aqueous solution which has exited the back taper 17 formed by the welding seam 15 and flows along the catheter 3. The second welding seam 16 helps in guiding the aqueous wetting medium 4 to and along the catheter 3. Thus, the wetting medium 4 comes into contact with the hydrophilic outer surface 5 of the catheter 3 and activates the hydrophilic outer surface 5.

Figure 4C:
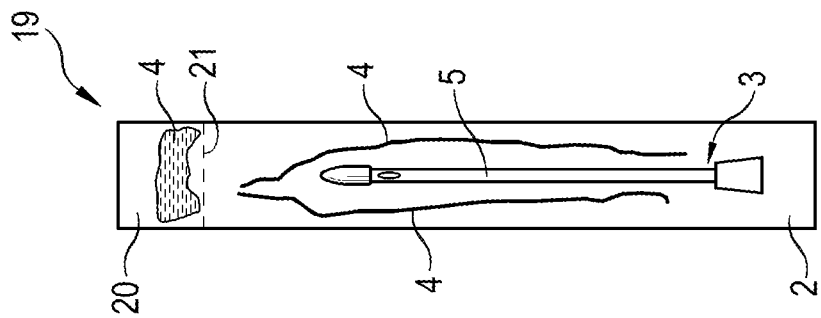
FIG. 4c shows the catheter assembly of FIG. 4a during activation of the hydrophilic outer surface of the catheter.
Figure 4B:
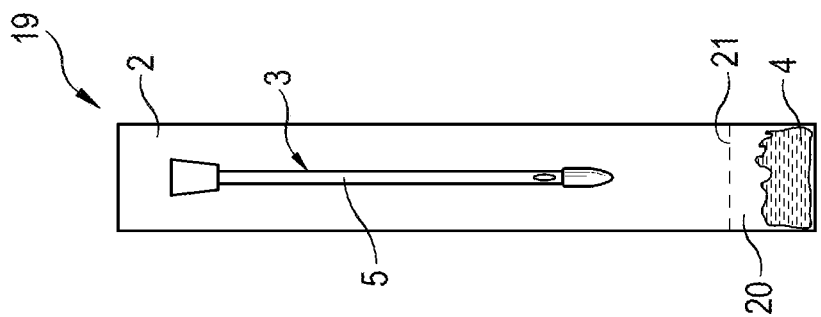
FIG. 4b shows the catheter assembly of FIG. 4a after the radiation treatment and before activation of the hydrophilic outer surface of the catheter.
Figure 4A:
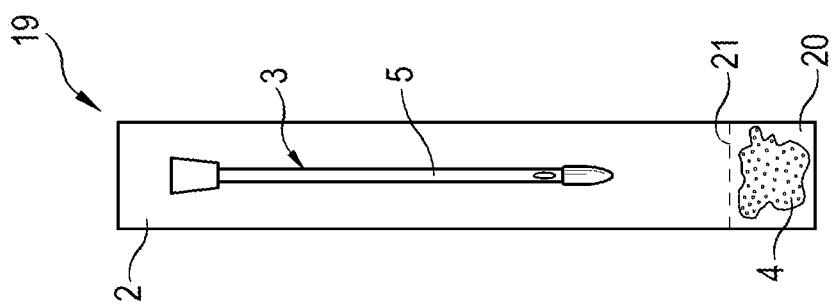
FIG. 4a shows a fourth embodiment of a catheter assembly before a treatment with electro-magnetic and/or particle radiation.

FIG. 4a shows a fourth embodiment of a catheter assembly 19. The same reference numbers are used for the same elements as described for the three previous embodiments. Catheter assembly 19 comprises a catheter package 2 and a catheter 3 arranged in the catheter package 2 as well as a wetting medium 4 also arranged in the catheter package 2. The wetting medium 4 is in its high viscosity state and is arranged at the bottom of the catheter package 2.

The catheter 3 is arranged above the bottom of the catheter package 2 so that the hydrophilic outer surface 5 of the catheter 3 is not in contact with the wetting medium 4. The catheter package 2 comprises a perforated lining 21 which forms a compartment 20 for the wetting medium 4. The perforated lining 21 can be made by welding separate points of the catheter package 2.

FIG. 4c shows the catheter assembly 19 of FIG. 4a after the radiation treatment and during activation of the hydrophilic outer surface 5 of the catheter 3. The wetting medium 4 has degraded and is now in its relatively fluid state. The catheter package 2 has been turned around 180° so that the wetting medium 4 follows the force of gravity in a downwards direction and therefore flows along the longitudinal direction of the catheter 3, comes into contact with the hydrophilic outer surface 5 of the catheter 3 and thus activates the hydrophilic outer surface 5 of the catheter 3.

Figure 5C:
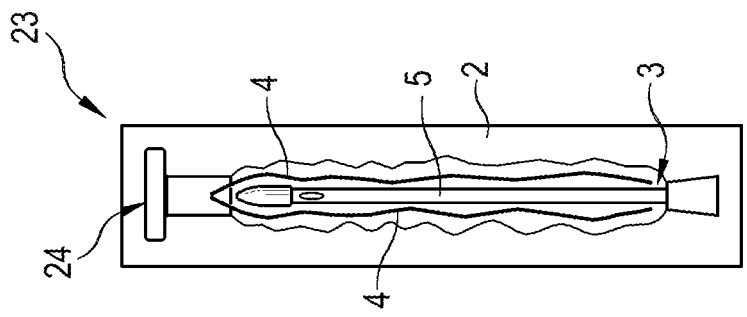
FIG. 5c shows the catheter assembly of FIG. 5a during activation of the hydrophilic outer surface of the catheter.
Figure 5B:
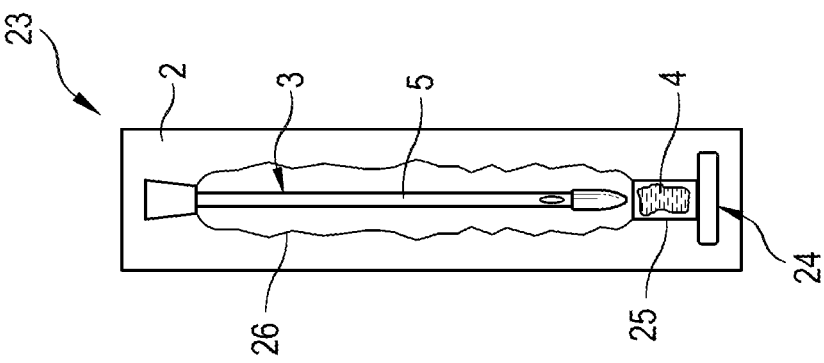
FIG. 5b shows the catheter assembly of FIG. 5a after the radiation treatment and before activation of the hydrophilic outer surface of the catheter.
Figure 5A:
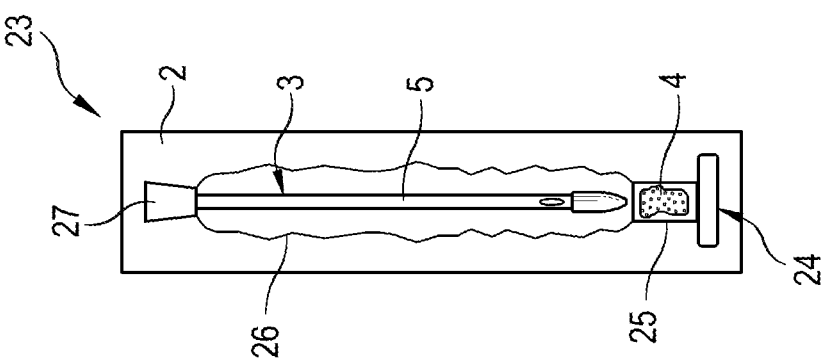
FIG. 5a shows a fifth embodiment of a catheter assembly before a treatment with electro-magnetic and/or particle radiation.

A fifth embodiment of a catheter assembly 23 is shown in FIG. 5a. The catheter assembly 23 comprises the catheter 3 and the wetting medium 4 which are both arranged in the catheter package 2 so that the wetting medium 4 is not in contact with the hydrophilic outer surface 5 of the catheter 3. The catheter assembly 23 further comprises an insertion aid 24. The insertion aid has a cylindrical body 25 which forms a compartment in which the wetting medium 4 is arranged. The insertion aid 24 further comprises a stopper at the side which comes into contact with the urethra when using the catheter. The insertion aid is formed in such a way that it can be easily gripped by a patient with reduced dexterity. The insertion aid 24 is connected to a thin sleeve 26 which extends along the length of the catheter 3 and is connected with a funnel 27 at the exterior end of the catheter 3.

FIG. 5c shows the catheter assembly 23 after the radiation treatment and during activation of the hydrophilic outer surface 5 of the catheter 3. The wetting medium 4 now has a low viscosity. The whole catheter package 2 has been turned around so that the wetting medium 4 flows downwardly along the longitudinal direction of the catheter 3 and thus comes into contact with and activates the hydrophilic outer surface 5 of the catheter 3. The sleeve 26 guides the wetting medium along the catheter 3. In this way, it can be ensured that the complete area of the hydrophilic outer surface 5 of the catheter 3 is brought into contact with the wetting medium 4 and a complete activation of the hydrophilic outer surface 5 can be guaranteed.

Figure 6C:
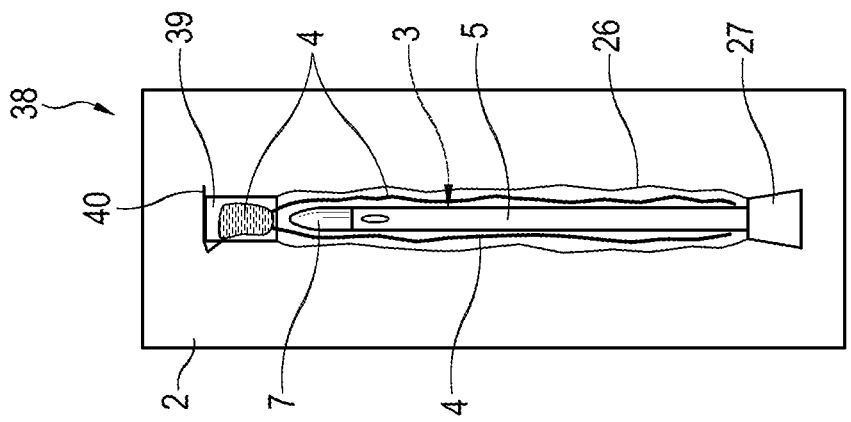
FIG. 6c shows the catheter assembly of FIG. 6a during activation of the hydrophilic outer surface of the catheter.
Figure 6B:
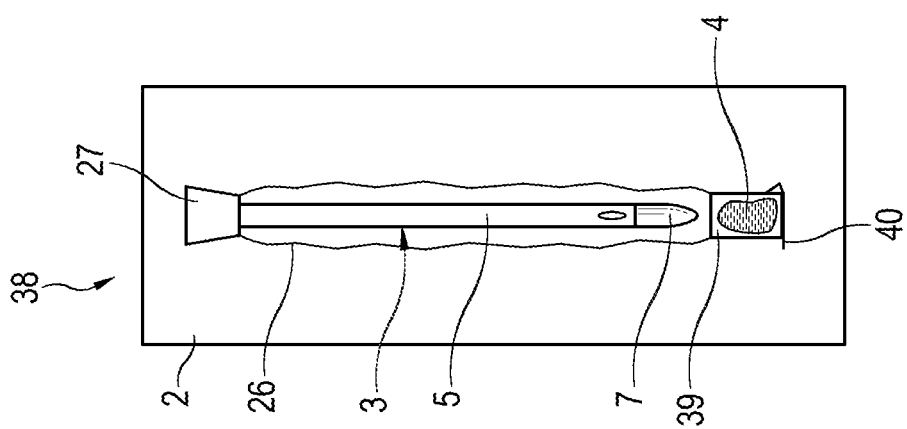
FIG. 6b shows the catheter assembly of FIG. 6a after the radiation treatment and before activation of the hydrophilic outer surface of the catheter.
Figure 6A:
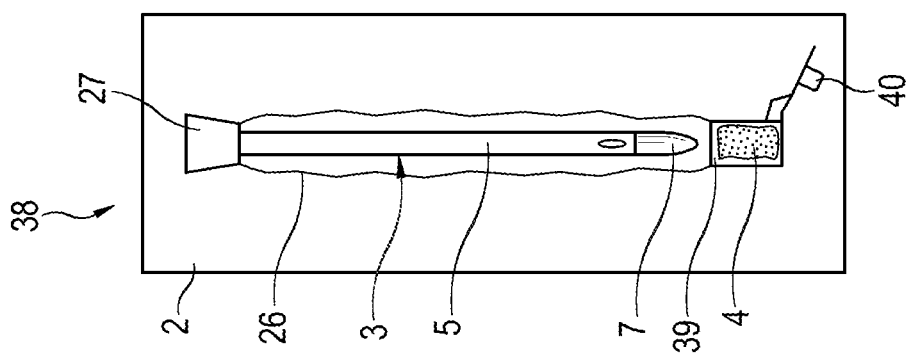
FIG. 6a shows a sixth embodiment of a catheter assembly before a treatment with electro-magnetic and/or particle radiation.

FIG. 6a shows a sixth embodiment of a catheter assembly 38. The same elements as described in the previous embodiments are referred to with the same reference numbers. Catheter assembly 38 comprises a catheter package 2, in which a catheter 3 with an inactivated hydrophilic outer surface 5 and a wetting medium 4 are arranged. One end of the catheter 3 is provided with a catheter tip 7 for insertion into the urethra of a patient, the other end of the catheter 3 is provided with a funnel 27. The wetting medium 4 is arranged in a compartment 39 which is arranged in front of the catheter tip 7 and which can be closed with a cap 40. Cap 40 is hingedly connected to the compartment 39. The funnel 27 is connected to a sleeve 26 which extends along the complete length of the catheter 3. Near the catheter tip 7, the sleeve 36 is connected to the compartment 39. When the compartment 39 is closed via the cap 40, the catheter 3 is completely surrounded by the sleeve 26 and the compartment 39 with the cap 40.

FIG. 6c shows the catheter assembly 38 after the radiation treatment and during activation of the hydrophilic outer surface 5 of the catheter 3. The wetting medium 4 is now in its low viscosity state and can therefore easily flow along the catheter 3. In order to bring the wetting medium 4 in contact with the hydrophilic outer surface 5 of the catheter 3, the catheter package 2 is turned around 180° so that the wetting medium 4 in its low viscosity state flows out of the compartment 39, passes the catheter tip 7 and flows downward along the surface of the catheter 3. Due to the sleeve 26, the wetting medium 4 is guided closely along the catheter 3 and does not flow through the complete packaging 2. The cap 40 of the compartment 39 ensures that no wetting medium 4 exits the compartment 39 in the wrong direction. The compartment 39 can serve as an insertion aid when catheter 3 is used.

A further embodiment of a catheter assembly 42 is shown in FIG. 7a. The same elements as described in the previous embodiments are referred with the same reference numbers. Catheter assembly 42 also comprises a catheter package 2 with a catheter 3 with an inactivated hydrophilic outer surface 5 and a wetting medium 4. The catheter 3 comprises a funnel 43 at one end. The funnel 43 can be closed with a cap 44, which is hingedly connected to the funnel 43. At the other end of the catheter 3, that is, near the catheter tip 7, an insertion aid 24 is arranged. The whole catheter 3 is surrounded by a thin sleeve 26. One end of this sleeve 26 is connected to the funnel 43, the other end of this sleeve 26 is connected to the insertion aid 24. The wetting medium 4 is arranged in the insertion aid 24.

FIG. 7c shows the catheter assembly 42 after the radiation treatment and during activation of the hydrophilic outer surface 5 of the catheter 3. For activating the hydrophilic outer surface 5 of the catheter 3, it is brought into contact with the wetting medium 4. During the radiation treatment, the wetting medium has reduced its viscosity and is now in its low viscosity state. The catheter package 2 has been turned around 180°, so that the insertion aid 24 with the wetting medium 4 arranged therein is now above the catheter 3. The wetting medium 4 follows the force of gravity and flows downward on the surface of the catheter 3 and thus comes into contact with the hydrophilic coating 5. The sleeve 26 guides the wetting medium 4 closely along the catheter 3. The wetting medium 4 can flow through the eyes 45 of the catheter 3 to the interior of the catheter 3. In order to prevent leakage of the wetting medium 4 past the funnel 43, the cap 44 is closed and the wetting medium 4 stays inside the catheter 3.

Figure 8C:
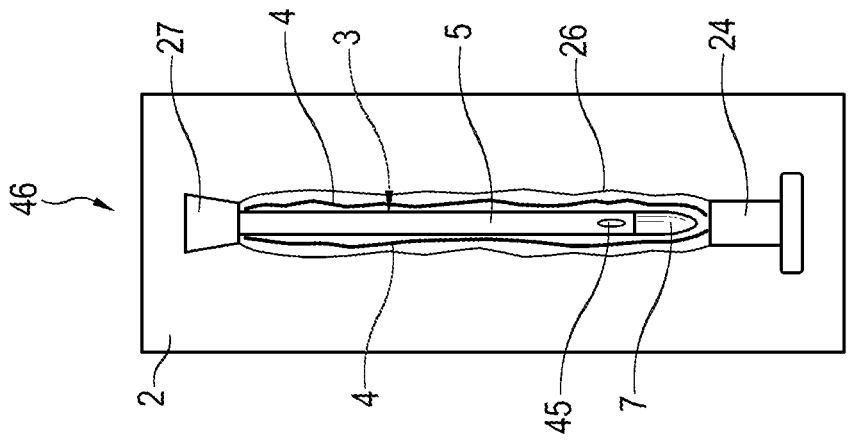
FIG. 8c shows the catheter assembly of FIG. 8a during activation of the hydrophilic outer surface of the catheter.
Figure 8B:
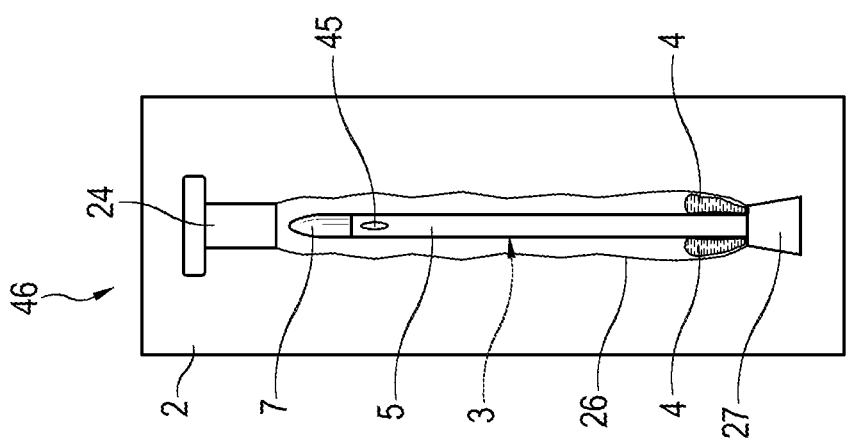
FIG. 8b shows the catheter assembly of FIG. 8a after the radiation treatment and before activation of the hydrophilic outer surface of the catheter.
Figure 8A:
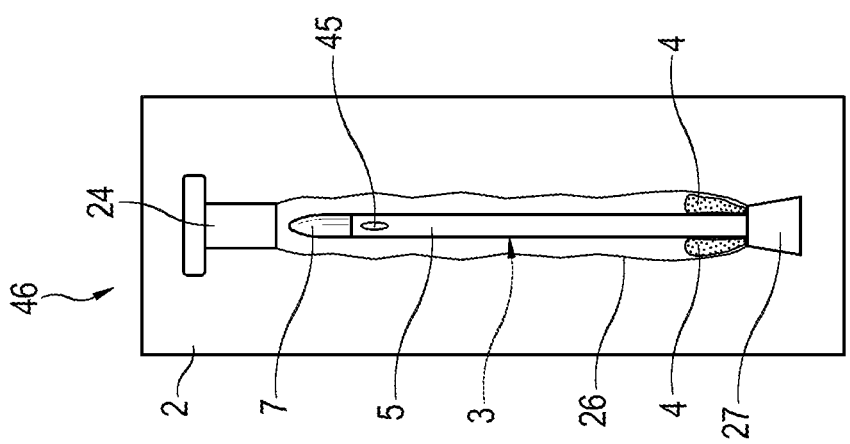
FIG. 8a shows an eighth embodiment of a catheter assembly before a treatment with electro-magnetic and/or particle radiation.

FIGS. 8a to 8c show an eighth embodiment of a catheter assembly 46. As with all previous embodiments, the same elements as described in the previous embodiments are referred with the same reference numbers. The catheter assembly 46 also comprises a catheter 3 with an inactivated hydrophilic outer surface 5 at least along its insertable length and a wetting medium 4 which are arranged in a catheter package 2. As shown in FIG. 8a, the wetting medium 4 is placed in the catheter package 2 so that it does not come into contact with the hydrophilic parts of the catheter 3. The catheter 3 comprises a funnel 27 arranged at one end of the catheter and a catheter tip 7 for introducing the catheter in a urethra of a user on the other end of the catheter 3. Near the catheter tip 7 an insertion aid 24 is arranged. A thin sleeve 26 is placed around the catheter 3 and is connected at one end with the funnel 27 and at other end with the insertion aid 24. The catheter 3 is arranged in the catheter package 2 in such a way that the funnel 27 is arranged near the bottom of the catheter package 2. The wetting medium 4 is arranged inside the sleeve 26 near the funnel 27 near an uncoated section of the catheter 3.

FIG. 8c shows the catheter assembly 46 after the radiation treatment and before activation of the hydrophilic outer surface 5 of the catheter 3. During radiation, the wetting medium 4 has experienced a decrease in viscosity and is now in a low viscosity state. The catheter package 2 has been turned around 180°, so that the wetting medium 4 flows downward along the catheter 3 following the force of gravity. The sleeve 26 guides the wetting medium 4 in close proximity to the shaft of catheter 3 so that it comes into contact with the hydrophilic outer surface 5 and activates the hydrophilic outer surface 5. As the wetting medium 4 is placed near the funnel 27 at the beginning, it does not directly flow into the eyes 45 of the catheter and out of the funnel 27 without activating the hydrophilic outer surface 5 of the catheter 3.

FIG. 9a shows a ninth embodiment of a catheter assembly 29. The same elements as described in the previous embodiments are referred to with the same reference numbers. Catheter assembly 29 comprises a catheter package 2, a catheter 3 with a hydrophilic outer surface 5 and a wetting medium 4. The wetting medium 4 is placed at one end of the catheter package and the catheter 3 is placed at the opposite end of the catheter package 2. A physical barrier 30 is fixed to the catheter package 2 between the wetting medium 4 and the catheter 3. The physical barrier 30 can for example be a clip or a fastener device. In the state of the catheter assembly 29 as shown in FIG. 9a, the wetting medium 4 does not come into contact with the hydrophilic outer surface 5 of the catheter. FIGS. 9b and 9c shows the catheter assembly 20 of FIG. 9a after the radiation treatment and during activation of the hydrophilic outer surface 5 of the catheter 3. The physical barrier 30 has been removed from the catheter package 2 so that the wetting medium 4 which has dissociated during the radiation treatment and is now in its rather liquid state with a low viscosity, can flow freely through the interior of the catheter package 2 and thus comes into contact with the hydrophilic outer surface 5 of the catheter 3.

In the embodiments 1 to 9 as described above the wetting medium 4 can be a gel which experiences a non-reversible decrease in viscosity when energy is brought into the system, for example via electro-magnetic and/or particle radiation. The gel then transforms into an aqueous solution which flows through the catheter package 2 and thus activates the hydrophilic outer surface 5 of the catheter 3. The wetting medium 4 therefore directly activates the hydrophilic outer surface 5 of the catheter 3 at least along its insertable length. It is also possible to use viscoelastic fluids, Bingham fluids, pseudoplastic fluids, dilatant fluids or Newtonian fluids as wetting medium as long as they experience a decrease in viscosity when submitted to external effects. It is also possible that the wetting medium changes its state of matter during the radiation treatment from a solid to a liquid state. In this context, solid state means that the material has a definite shape and volume. Liquid state means that the material has a definite/constant volume and a shape that conforms to the shape of its container.

Figure 10A:
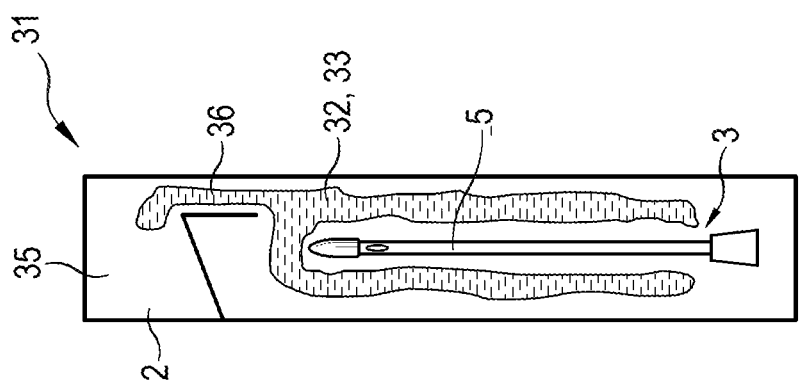
FIG. 10a shows a tenth embodiment of a catheter assembly before a treatment with electro-magnetic and/or particle radiation.
Figure 10B:
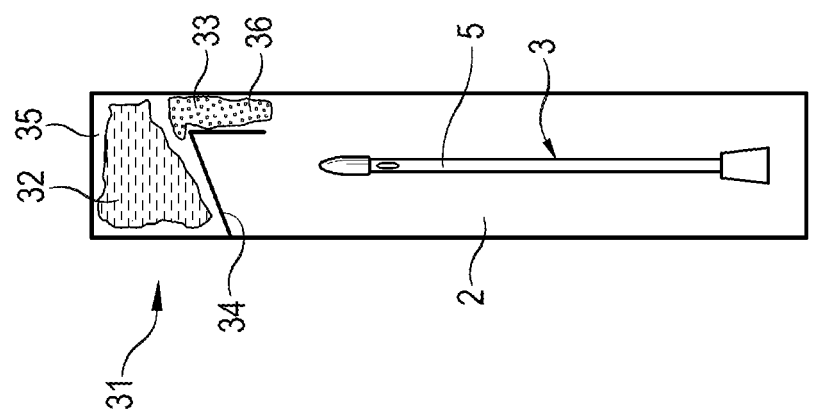
FIG. 10b shows the catheter assembly of FIG. 10a after the radiation treatment and during activation of the hydrophilic outer surface of the catheter.

In the embodiments as shown in FIGS. 10a and 10b, the wetting medium is partly formed of a gel 33 and partly of an aqueous solution 32. In this tenth embodiment of a catheter assembly 31, the same reference numbers as used in the description of the previous embodiments are used for the same elements as shown before. The catheter assembly 31 comprises a catheter package 2, a catheter 3 with an inactivated hydrophilic outer surface 5 and a wetting medium 32, 33. The catheter package 2 is provided with a welding seam 34 which forms a back taper 35 in the catheter package which is connected to the remaining part of the catheter package 2 via a small channel 36.

The wetting medium is partly formed of an aqueous solution 32 and partly of a gel-like system 33. The gel 33 is arranged in the channel 36 and thus forms a plug which holds the aqueous solution 32 in the back taper 35. The aqueous solution 32 can thus not exit the back taper 35 and is separated from the hydrophilic outer surface 5 of the catheter 3.

FIG. 10b shows the catheter assembly 31 of FIG. 10a after the radiation treatment and during activation of the hydrophilic outer surface 5 of the catheter 3. The gel 32 has at least partly dissociated to let the aqueous solution 32 pass. The aqueous solution 32 flows downwardly and is now in contact with the hydrophilic outer surface 5 of the catheter 3 and activates the hydrophilic outer surface 5.

In the following, methods for making the ready-to-use catheter assembly as described above are explained in detail.

FIG. 1a shows the catheter assembly 1 before treatment with electro-magnetic and/or particle radiation. The wetting medium 4 is a gel-like system and is in a relatively solid state with a high viscosity so that it exhibits little or no viscous flow. However, as already mentioned above, the wetting medium can be any liquid which reduces its viscosity when external conditions are changed. Examples for such liquids are viscoelastic fluids, Bingham fluids, pseudoplastic fluids, dilatant fluids or Newtonian fluids. The wetting medium can also initially be a solid that changes its state of matter during the radiation treatment from the solid state to to the liquid state. The definition of "solid state" and "liquid state" can be found above. The wetting medium 4 can also be a gel containing a solute polymer, for example Carboxymethyl Cellulose. Other gels, hydrogels or high viscous aqueous solutions which contain a polymer or a thixotropic agent are also possible. The wetting medium 4 is arranged at one end (the bottom) of the catheter package 2 and the inactivated hydrophilic outer surface 5 of the catheter 3 is arranged at the end of the catheter package so that it is not in contact with the wetting medium 4. In this position, gravity facilitates the separation of the catheter 3 and the wetting medium 4.

FIG. 1b shows the catheter assembly 1 during a treatment with electro-magnetic and/or particle radiation of the whole assembly. During the radiation treatment, the catheter package 2 remains in the same position as shown in FIG. 1a. The preferred form of radiation is gamma radiation. However, other forms of radiation, i.e. beta radiation, x-ray or UV radiation are possible. The level of radiation lies above the natural background radiation and is high enough so that the viscosity of the wetting medium 4 decreases to allow an activation of the hydrophilic coating. Preferably, the treatment with the electro-magnetic and/or particle radiation is a sterilization step for the whole catheter assembly. The wetting medium 4 can for example be a rigid gel or a hydrogel which comprises a solute polymer in an aqueous solution.

The wetting medium 4 reduces viscosity during electro-magnetic and/or particle radiation. In FIG. 1b, the wetting medium 4 is shown in its liquid state. The wetting medium 4 has flown to the lower end of the package 2 and remains there separated from the hydrophilic outer surface 5 of the catheter 3 at least along its insertable length.

FIG. 1c shows the activation of the catheter 3. The whole catheter package 2 is turned around 180° so that the bottom of the catheter package 2 which initially contained the wetting medium 4 is on the top. Following gravity, the wetting medium 4 flows downwardly and comes into contact with the hydrophilic outer surface 5 of the catheter 3. In this way, the hydrophilic outer surface 5 of the catheter 3 is activated. As the welding seam 8 tapers towards the catheter tip 7 and the wetting medium 4 is guided along the catheter 3 it comes into intimate contact with the hydrophilic outer surface 5 and ensures a good activation.

The method for making a ready-to-use catheter assembly according to the second embodiment for the catheter assembly 10 as shown in FIGS. 2a to 2d functions basically as described above. In FIG. 2a, the catheter assembly 10 is shown before the radiation treatment. The wetting medium 4 is still in its relatively high viscosity state and is arranged in the back taper 12 at the bottom of the catheter package 2. The catheter 3 with its inactivated hydrophilic outer surface 5 is arranged above the wetting medium 4 and is separated from the wetting medium 4 by the welding seam 11. FIG. 2b shows the treatment of the catheter assembly 10 with electro-magnetic and/or particle radiation. Preferably, this step is a radiation sterilization, preferably by gamma sterilization as described above and the wetting medium 4 is a gel which experiences a non-reversible decrease in viscosity when submitted to electro-magnetic and/or particle radiation. The wetting medium 4 therefore dissociates during radiation and flows along the bottom of the package 2, guided by the welding seam 11.

FIGS. 2c and 2d show the activation of the hydrophilic outer surface 5 of the catheter 3. In a first step, as shown in FIG. 2c, the catheter package 2 is rotated around an angle of 90°. The wetting medium 4 flows out of the back taper 12 and follows the welding seam 11 through the top of the catheter package. In the second step, as shown in FIG. 2d, the catheter package 2 is rotated around an angle of 180° so that the wetting medium 4 is now in contact with the hydrophilic outer surface 5 of the catheter 3 and thus activates the hydrophilic outer surface 5.

FIGS. 3a to 3d show the radiation treatment and the activation of the catheter assembly 14 according to the third embodiment. FIG. 3a shows the catheter assembly 14 before radiation treatment. The wetting medium 4 is arranged in the back taper 15 at the bottom of the catheter package 2 and has a high viscosity. In FIG. 3b, the radiation treatment is shown. The complete catheter assembly 14 is submitted to electro-magnetic and/or particle radiation, preferably gamma radiation. Preferably, the complete assembly is sterilized in this step. During the radiation treatment, the wetting medium 4 decreases in viscosity as described in the first embodiment and turns into aqueous solution. As the catheter package 2 remains in the position as shown in FIG. 3a, the wetting medium 4 remains at the bottom of the catheter package 2.

FIG. 3c shows the first step of activating the hydrophilic outer surface 5 of the catheter 3. The catheter package 2 is rotated around an angle of 90° and the wetting medium 4 flows along the welding seam 15 out of the back taper 17 in the direction of the catheter 3. The catheter package 2 is then again rotated around an angle of 90° (see FIG. 3d) and the wetting medium 4 flows downwardly along the welding seam 16 and comes into contact with the catheter 3 and thus activates the hydrophilic outer surface 5 of the catheter 3.

FIGS. 4a to 4c show the method for a radiation treatment and an activation for the fourth embodiment of the catheter assembly 19. In FIG. 4a, the catheter assembly 19 is shown before the radiation treatment. The wetting medium 4 is still in its high viscosity state and remains at the bottom of the catheter package 2 separated from the catheter 3 with the hydrophilic outer surface 5 via gravity. In FIG. 4b, the complete catheter assembly is irradiated with electro-magnetic and/or particle radiation, for example sterilized via radiation sterilization. Due to the radiation treatment, the wetting medium 4 reduces viscosity and turns into an aqueous solution. The catheter package 2 remains in the position as shown in FIG. 4a. In FIG. 4c, the catheter package 2 is rotated around an angle of 180° and the wetting medium 4 flows through the perforated lining 21 downwardly and comes into contact with the hydrophilic outer surface 5 of the catheter 3 and thus activates the hydrophilic outer surface 5.

The same method is shown in FIGS. 5a to 5c for the fifth embodiment of the invention. In this embodiment, the wetting medium 4 is arranged in the insertion aid 25. In FIG. 5a, which shows the catheter assembly 23 before the radiation treatment, the wetting medium 4 and the catheter 3 with its inactivates hydrophilic outer surface 5 are separated from each other. In FIG. 5b, the whole catheter assembly 23 is submitted to gamma radiation so that the assembly is sterilized and the wetting medium 4 degrades into an aqueous solution. After that, the catheter package 2 is rotated around an angle of 180° as shown in FIG. 5c. The wetting medium 4, which now has a low viscosity, flows downwardly along the catheter 3 and comes into contact with the hydrophilic outer surface 5 of the catheter 3 and activates the hydrophilic outer surface 5.

FIGS. 6a to 6c show the method for making the catheter assembly 38 according to the sixth embodiment of the invention. FIG. 6a shows the catheter assembly 38 before the radiation treatment. The wetting medium 4 is still in its high viscosity state and placed in the compartment 39 which is arranged below the catheter 3 with the hydrophilic outer surface 5.

FIG. 6b shows the complete catheter assembly 38 during the radiation treatment. The complete catheter assembly 38 is submitted to electro-magnetic or particle radiation and is thereby sterilized. Due to the radiation, the wetting medium 4 reduces its viscosity and turns into its low viscosity state. The catheter assembly 38 is still in its first position wherein the compartment 39 with the wetting medium 4 is arranged below the catheter 3.

FIG. 6c shows the activation of the hydrophilic outer surface 5 of the catheter 3. The complete catheter assembly 38 is turned around 180° so that the compartment 39 with the wetting medium 4 is now arranged above the catheter 3. Following the force of gravity, the wetting medium 4 in its low viscosity state flows downwards along the catheter 3. The sleeve 26 guides the wetting medium 4 closely along the catheter 3 with the hydrophilic outer surface 5. Thereby, the hydrophilic outer surface 5 of the catheter 3 comes into contact with the wetting medium medium 4 and is activated. When the compartment 39 is closed with the hinge cap 40, the catheter 3 is completely sealed in the sleeve 26.

FIGS. 7a, 7b and 7c show the activation of the hydrophilic outer surface 5 of the catheter 3 for the seventh embodiment of the invention. FIG. 7a shows the catheter assembly 42 before the radiation treatment. The catheter 3 is arranged in the catheter package 2 so that the catheter tip 7 faces the bottom of the catheter package 2. The wetting medium 4 is arranged in the insertion aid 24 and thus arranged below the catheter 3 with the hydrophilic outer surface 5. The funnel 43 can be closed with the cap 44 to prevent leakage of the wetting medium 4.

FIG. 7b shows the catheter assembly 42 during and after the radiation treatment but before activation of the hydrophilic outer surface 5 of the catheter 3. During the radiation treatment, the wetting medium 4 turns into its low viscosity state due to the energy provided by the radiation. As the wetting medium 4 is arranged near the bottom of the catheter package 2, it remains there also in its low viscosity state. The wetting medium 4 and the hydrophilic outer surface 5 of the catheter 3 thus do not come into contact. In order to activate the hydrophilic outer surface 5 of the catheter 3, the catheter assembly 42 is rotated around an angle of 180° as shown in FIG. 7c. The wetting medium 4 in its low viscosity state is guided by the sleeve 26 downwardly along the catheter 3, comes into contact with the hydrophilic outer surface 5 and activates the hydrophilic outer surface 5. As the funnel 43 is closed by the cap 44, the wetting medium 4 cannot exit and leakage is prevented.

FIGS. 8a, 8b and 8c show the activation method for the eight embodiment of the invention. FIG. 8a shows the catheter assembly 46 before the radiation treatment. The catheter 3 with the sleeve 26 and the insertion aid 24 is arranged in the catheter package 2 so that the funnel 27 faces towards the bottom. The wetting medium 4 is placed inside the sleeve 26 near the funnel 27. The surface of the catheter 3 in the region where the wetting medium 4 is arranged does not need to be coated. During electromagnetic and/or particle radiation, the catheter package 2 remains in the position as shown in FIG. 8a. This is shown in FIG. 8b. Due to the energy submitted to the system during electro-magnetic and/or particle radiation, the wetting medium 4 reduces its viscosity and turns into its low viscosity state. Under the force of gravity, the wetting medium 4 stays near the funnel 27. As the catheter tip 7 is arranged at the top of the catheter package 2, the wetting medium 4 cannot flow through the eyes 45 of the catheter 3. For activating the hydrophilic outer surface 5 of the catheter 3, the complete catheter assembly 46 is rotated around 180° so that the funnel 27 is now above the catheter 3 and the catheter tip 7 faces the bottom. Following the force of gravity, the wetting medium 4 flows downwardly along the catheter 3, and thus comes into contact with and activates the hydrophilic outer surface 5 of the catheter 3. Due to this arrangement, it is thus prevented that after the radiation treatment, the wetting medium in its low viscosity state flows directly into the eyes 45 of the catheter and out of the funnel 27 without activating the hydrophilic outer surface 5.

In FIGS. 9a to 9c, the sterilizing method for the ninth embodiment of the invention is shown. FIG. 9a shows the catheter assembly 29 before the radiation treatment. The wetting medium 4 is still in its high viscosity state and is separated from the catheter 3 by a physical barrier 30. In FIG. 9b the complete catheter assembly is submitted to radiation and is thereby sterilized and the wetting medium 4 turns into an aqueous solution. The physical barrier 30 is then removed and the catheter package 2 is turned around an angle of 180° (see FIG. 6c). The wetting medium 4 flows along the catheter 3 thereby coming into contact with and activating the hydrophilic outer surface 5 of the catheter 3.

In all the embodiments as described above, the viscosity of the wetting medium 4 before the radiation treatment with electro-magnetic and/or particle radiation, that is the gel, is at least 7000 cP, preferably at least 25000 cP. During the radiation treatment, when the wetting medium 4 is submitted to electro-magnetic and/or particle radiation, the viscosity of the wetting medium 4 decreases by at least 80%, preferably at least 90%.

In a preferred embodiment for the wetting medium 4, the viscosity of the wetting medium after the treatment with electro-magnetic and/or particle radiation is smaller than 1000 cP, preferably smaller than 100 cP. The viscosity of the wetting medium (gel) was measured using a Brookfield viscometer. The sample was placed below the spindle and the spindle was lowered into the sample to a set point.

The spindle rotates at a specific speed (30 rpm) and the resistance of the gel correlates to the viscosity. The spindle used was LV4, #64. The temperature at the test was 25° C.

In FIGS. 10a and 10b, the wetting medium (gel) is used as an activation aid and forms a plug 33 for an aqueous solution 32 before the radiation treatment (see FIG. 10a). During the radiation treatment the gel 33 reduces viscosity sufficiently, flows downwardly in the direction of the catheter 3 together with the aqueous solution 32 so that at least the aqueous solution 32 comes into contact with the hydrophilic outer surface 5 of the catheter 3 and thus activates the catheter 3. Before the radiation treatment, the viscosity of the gel 33 is at least 7000 cP. In this embodiment, a viscosity decrease due to the radiation treatment with electro-magnetic and/or particle radiation of approximately 10% is sufficient, because the plug formed by the gel 33 only needs to deform to let the aqueous solution 32 pass. The viscosity of the gel 33 is determined as described for the previous embodiments.

The methods for making the ready-to-use catheter assembly are described only for a wetting medium which initially is in the form of a gel. As described earlier, the wetting medium can be any liquid which reduces its viscosity when external conditions are changed, for example viscoelastic fluids, Bingham fluids, pseudoplastic fluids, dilatant fluids or Newtonian fluids. It is also possible to use a wetting medium which initially is a solid and which experiences a change of state of matter during the radiation treatment from the solid state to the liquid state.

LIST OF REFERENCE NUMBERS

1: Catheter assembly
2: Catheter package
3: Catheter
4: Wetting medium
5: Hydrophilic outer surface
6: Sleeve
7: Catheter tip
8: Welding seam
10: Catheter assembly
11: Welding seam
12: Back taper
14: Catheter assembly
15: Welding seam
16: Welding seam
17: Back taper
19: Catheter assembly
20: Compartment
21: Perforated lining
23: Catheter assembly
24: Insertion aid
25: Cylindrical body
26: Sleeve
27: Funnel
29: Catheter assembly
30: Physical barrier
31: Catheter assembly
32: Wetting medium aqueous solution
33: Wetting medium gel
34: Welding seam
35: Back taper
36: Channel
38: Catheter assembly
39: Compartment
40: Cap
42: Catheter assembly
43: Funnel
44: Cap
45: Catheter eyes
46: Catheter assembly

The invention claimed is:

1. A method of making a ready-to-use catheter assembly comprising the following steps:
placing a catheter with an inactivated hydrophilic outer surface at least along its insertable length and a wetting medium in a catheter package, wherein the wetting medium is in a first state a gel comprising at least one polymer, and sealing the catheter package containing the catheter and wetting medium inside said catheter package,
after sealing the catheter package, sterilizing the catheter assembly inside said sealed catheter package by treating the catheter package with the catheter and the wetting medium as said gel in said first state with electro-magnetic and/or particle radiation while at least initially the hydrophilic outer surface at least along the insertable length of the catheter remains substantially inactivated, wherein the wetting medium decreases in viscosity such that the wetting medium transforms from the first state as said gel to a second state as a liquid when submitted to electro-magnetic and/or particle radiation,
activating the hydrophilic outer surface at least along the insertable length of the catheter with the wetting medium in said second state after treating the catheter package with the radiation,
wherein the gel has a viscosity greater than 7000 cP before the sterilizing of the catheter assembly by treating the catheter package with said radiation, and wherein the viscosity of the wetting medium decreases by at least 80% when submitted to said electro-magnetic and/or particle radiation.

2. The method according to claim 1, wherein the polymer is organic or synthetic carbohydrate or a lipid based polymer.

3. The method according to claim 1, wherein the radiation used for treating the catheter package is gamma radiation, x-ray, e-beam or ultra violet.

4. The method according to claim 1, wherein the energy dose of the radiation is in a range of 1 to 50 kGy, preferably 15 kGy to 45 kGy, more preferably 25 to 45 kGy.

5. The method according to claim 1, wherein the gel has a viscosity greater than 25000 cP before the sterilizing of the catheter assembly by treating the catheter package with said radiation.

* * * * *